United States Patent [19]

Koike et al.

[11] Patent Number: 5,543,113
[45] Date of Patent: Aug. 6, 1996

[54] GAS ANALYZING APPARATUS

[75] Inventors: Hideki Koike, Chikuzenda-machi; Kenji Takeda, Kyoto, both of Japan

[73] Assignee: Horiba, Ltd., Japan

[21] Appl. No.: 313,558

[22] Filed: Sep. 27, 1994

Related U.S. Application Data

[63] Continuation of Ser. No. 33,088, Mar. 16, 1993, abandoned.

[30] Foreign Application Priority Data

Mar. 21, 1992 [JP] Japan ............................ 4-023885 U
Mar. 21, 1992 [JP] Japan ............................ 4-023886 U

[51] Int. Cl.$^6$ .......................... G01N 7/00; G01N 30/02
[52] U.S. Cl. ........................... 422/83; 422/94; 422/95; 422/96; 422/97; 436/137; 73/23.21; 73/23.31
[58] Field of Search ......................... 73/23.21, 23.31; 356/438; 422/83, 94, 95, 96, 97; 436/137

[56] References Cited

U.S. PATENT DOCUMENTS

| | | | |
|---|---|---|---|
| 4,141,955 | 2/1979 | Obiaya | 422/95 |
| 4,379,402 | 4/1983 | Harman, III | 73/23 |
| 5,088,313 | 2/1992 | Fabinski et al. | 73/1 G |

FOREIGN PATENT DOCUMENTS

| | | | |
|---|---|---|---|
| 2445444 | 9/1973 | Germany . | |
| 2832296 | 7/1977 | Germany . | |
| 3204456 | 2/1982 | Germany | G01N 21/59 |
| 3413492 | 4/1984 | Germany | G01N 1/24 |
| 3707622 | 3/1987 | Germany | G01N 29/02 |
| 87302113 | 3/1987 | Germany | G01F 1/32 |
| 3800219 | 1/1988 | Germany | G01F 1/32 |
| 3837232 | 11/1988 | Germany | G01F 25/00 |
| 4-291141 | 10/1992 | Japan | G01N 27/16 |

OTHER PUBLICATIONS

German Publication: MTZ Motortechnisch Zeitschrift 52 (1991), pp. 356–361.

Primary Examiner—David A. Redding
Attorney, Agent, or Firm—Poms, Smith, Lande & Rose

[57] ABSTRACT

For an exhaust analyzer, the factors causing turbulence and mixing of the sample gas are removed from the sample gas-introducing pipe in order to introduce the sample gas into the analyzer cell under laminar conditions. Further, the indicated changes resulting from the fluctuations of sample gas pressure within the analysis cell of such a construction are compensated. As a result, the sample gas can be quantitatively analyzed with a high rate of response under the condition that the influences caused by the fluctuations of the sample gas pressure are reduced.

The sample gas is introduced into the cell-type gas analyzer from the sample gas source through a gas-introducing pipe under laminar conditions. A pressure sensor detects the changes in pressure within the cell of the gas analyzer, and in response to the pressure sensed by the pressure sensor a compensating means compensates for the erroneous indication of gas characteristics generated by the analysis cell as a result of the fluctuations of sample gas pressure therein.

10 Claims, 2 Drawing Sheets

GAS ANALYZING APPARATUS

This is a continuation of application(s) Ser. No. 08/033,088 field on Mar. 16, 1993 now abandoned.

BACKGROUND OF THE INVENTION

1. Field of the Invention

The present invention relates to a gas analyzing apparatus. More particularly, the present invention relates to a gas analyzing apparatus for introducing a sample gas from a source thereof into an analysis cell of the gas analyzer, and for compensating a pressure sensitivity of the analysis cell. By way of example, the gas analyzer may perform a quantitative analysis of the sample gas.

2. Description of the Prior Art

In order to conduct an analysis of the exhaust gas from an engine of an automobile under conditions such that the analysis is quick, it is remarkably important that the exhaust gas generated by a combustion cycle of the engine is immediately introduced into a gas analyzer. The exhaust gas from a particular combustion cycle must be introduced to the analyzer as it is so that the exhaust gas generated by the engine both before and after the particular combustion cycle is not mixed therewith.

Accordingly, a gas inlet port for an analysis cell of the gas analyzer has been brought as close as possible to an exhaust valve of the engine. The engine provides its exhaust gasses in pulses of gas flow. Thus, in the case where such a manner of introducing the exhaust gas to the analyzer is taken, if a gas pulse arrives at the inlet port of the analysis cell with a pressure of 1 Kgf/cm$^2$, for example, when a prevailing pressure in the cell is −0.4 Kgf/cm$^2$, the cell pressure rises to about −0.1 Kgf/cm$^2$.

Such a change in the pressure of the exhaust gas introduced into the analysis cell leads to a great fluctuation of an indicated quantitative value for the gas as a result of inherent pressure sensitivity of the analysis cell. Accordingly, in order to reduce the influence of such a fluctuation in pressure, conventional gas analyzers have been provided with a pair of pressure regulators 14, 15, as shown in FIG. 3, each branch-connected with a gas-introducing pipe 12 extending from the engine to an analysis cell 13 of the gas analyzer. The pressure regulators 14 and 15 are respectively connected upstream and downstream of the analysis cell 13 to primarily regulate a pressure within the cell. By operation of the pressure regulator 14 upstream of the analysis cell, and simultaneous operation of the pressure regulator 15 on the downstream side when the pressure within the cell cannot be sufficiently regulated by regulator 15 alone, a reduction is provided in the pressure fluctuations within the cell to about 3%, for example, of that otherwise experienced from a change in inlet pressure from 0 Kgf/cm$^2$ to 1 Kgf/cm$^2$.

However, problems have occurred with the conventional gas analyzers because the gas-introducing pipe 12 is changed in sectional shape at the branch connection of the pressure regulator 14 on the upstream side of the analysis cell 13. This change in cross sectional shape turns the exhaust gas introduced into the gas analyzer 13 from a laminar condition into a turbulent condition. Also contributing to this change of the exhaust gas to a turbulent condition is a retention of some of the exhaust gas in a branch pipe 16 leading toward the pressure regulator 14. Because of the volume of this branch pipe 16, some of the exhaust gas generated by the engine before and after a particular combustion cycle is retained and is mixed in with the exhaust gas generated by the particular combustion cycle, and the latter exhaust gas cannot be quantitatively analyzed.

SUMMARY OF THE INVENTION

In view of the above, the present invention is provided to achieve a gas analyzing apparatus capable of a high-speed response by an art different than the conventional pressure-regulating means.

In order to achieve the above described object, a gas-analyzing apparatus according to the present invention is characterized in that a sample gas is introduced into a cell-type gas analyzer from a sample gas source through a gas-introducing pipe under the laminar condition, the gas-introducing pipe is free of branch connections and volumes which could retain a contaminating portion of gas from before or after a particular combustion cycle, for example, a sensor detects changes in pressure within an analysis cell of the analyzer, and compensating means responsive to the detected pressure changes generated by fluctuations in pressure of the sample gas is provided to compensate these pressure changes.

That is to say, since the indicated changes generated by the fluctuations of pressure within the analysis cell are electrically compensated, and a branched pipe causing a retention and a turbulence of sample gas is not connected with the gas-introducing pipe, the sample gas can be introduced into the gas analyzer under the laminar condition, and the exhaust gas generated before and after a particular combustion cycle, for example, can be surely prevented from mixing in with the exhaust gas generated by the particular combustion cycle of the engine.

DETAILED DESCRIPTION OF THE PREFERRED EMBODIMENTS

Figure 1:
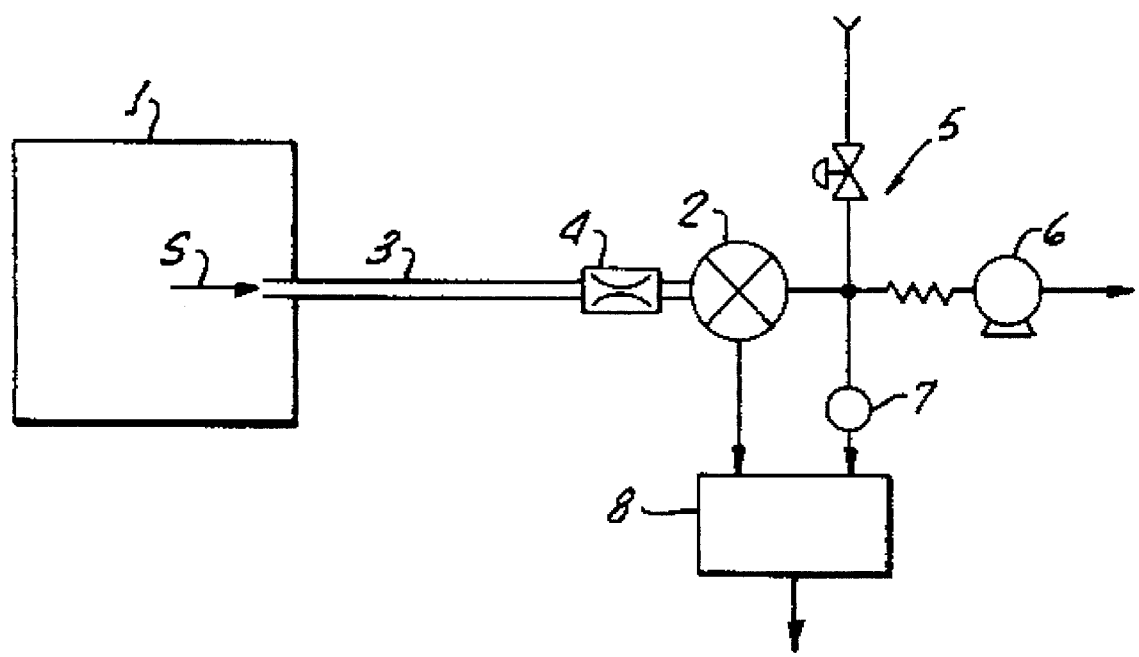
FIG. 1 is a diagram showing a principle of a gas-analyzing apparatus according to the present invention.
Figure 2:
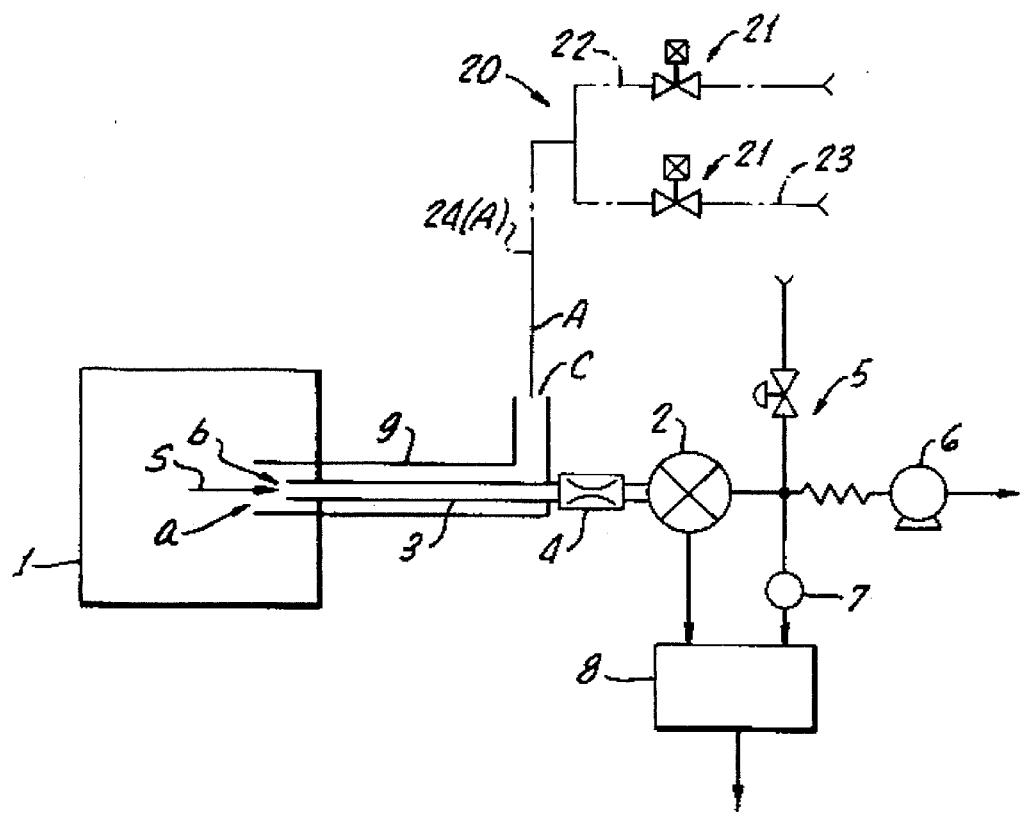
FIG. 2 is a diagram showing a principle of said gas-analyzing apparatus provided with calibration gas-introducing means according to another preferred embodiment.

The preferred embodiments of the present invention will be below described with reference to the drawings. FIG. 1 is a diagram showing a principle of a gas-analyzing apparatus with, for example, an exhaust gas 'S' from an automobile engine 1 as an object to be analyzed. Referring to FIG. 2, reference numeral 1 designates such an automobile engine as a sample gas source and reference numeral 2 designates an analysis cell of a cell-type gas analyzer for quantitatively analyzing the exhaust gas (sample gas) 'S' exhausted from the engine 1.

Figure 3:
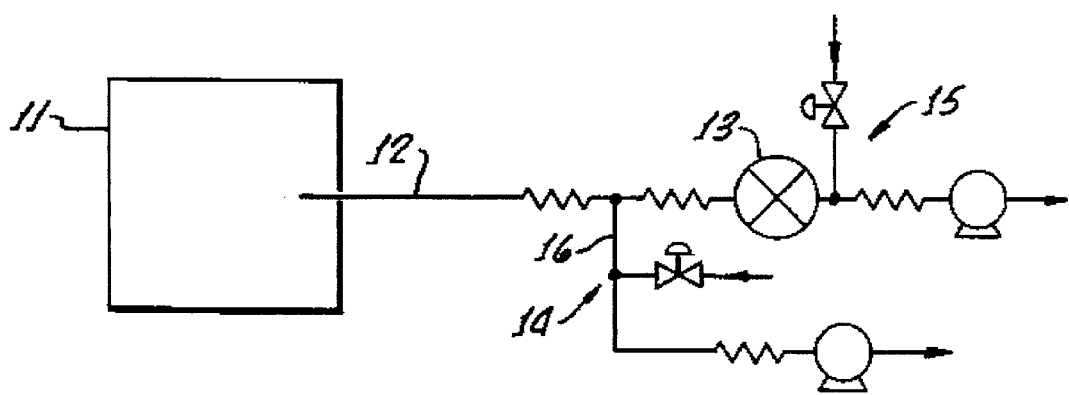
FIG. 3 is a diagram showing a principle of the conventional gas-analyzing apparatus.

Reference numeral 3 designates a gas-introducing pipe for introducing the exhaust gas 'S' into the gas analyzer cell 2, and the gas-introducing pipe 3 is provided with a venturi tube 4 so that it may be brought as close as possible to a gas inlet port of the gas analyzer cell 2. Further, the gas-introducing pipe 3 is reduced in length to bring the gas inlet port of the gas analyzer cell 2 as close as possible to an exhaust valve of the engine 1. Importantly, the gas-introducing pipe 3 is formed of a straight pipe free of branch connections and other changes of sectional shape, other than the venturi tube 4, which may moderate some of the inherent pressure fluctuations of the exhaust gas flow from the engine 1. This gas-introducing pipe 3 is also free of connected retention volumes, such as the branch pipe 16 of the conventional gas analyzer seen in FIG. 3. As a result, the exhaust gas 'S' exhausted from the engine 1 may be immediately introduced into the gas analyzer cell 2 under the laminar condition. This mode of introducing the exhaust gas 'S' into the gas analyzer cell 2 eliminates mixing of the exhaust gas generated by a particular combustion cycle of the engine 1 with the exhaust gas generated before and after the particular combustion cycle.

However, those ordinarily skilled in the pertinent arts will recognize that the analysis cell 13 of the conventional analyzer will have an output to an indicating device. The inherent pressure-responsive nature of the analysis cell 13 was described above in connection with the conventional expedient of using pressure regulators 14 and 15 to isolate the cell 13 from pressure fluctuations. However, the present invention avoids the use of a pressure regulator upstream of the analysis cell, and also avoids the problems such a pressure regulator causes. However, as is more particularly explained below, if the inherent pressure-responsiveness of the analysis cell 13 were not accounted for, the indicator which is to provide an indication of the quantitative analysis of the sample gas would also include an error because of this pressure responsiveness of the analysis cell.

Referring once again to FIG. 2, reference numeral 5 designates a cell pressure regulator connected with a passage on an exhaust side of the analysis cell 2 of an exhaust gas analyzer, while the reference numeral 6 designates a sample-suctioning pump. The reference numeral 7 designates a pressure sensor detecting a change in pressure within the analysis cell 2 of the gas analyzer, and reference numeral 8 designates an electrical compensating circuit which in response to the output of the pressure sensor 7 compensates for a change in the indicated quantitative analysis, for example, generated by or resulting from the change in pressure within the cell 2.

On FIG. 1, the output of the pressure sensor 7 to compensating circuit 8 is indicated by an appropriate arrow. Similarly, the output of the analysis cell 2 is represented by an appropriate arrow extending to compensating circuit 8. The compensating circuit 8 provides an output to an indicating device, not shown on the drawing Figs., but which will be familiar to those ordinarily skilled in the pertinent arts. This output of the compensating circuit 8 is also indicated by an appropriate output arrow on FIG. 1. The output of compensating circuit 8 is compensated for the inherent pressure sensitivity of the analysis cell 2, as is more fully explained.

According to the above described construction, not only the gas-introducing pipe 3 is formed of straight pipe but also the gas-introducing pipe 3 is not provided with a branched connecting portion of a pressure regulator causing a retention and a turbulence of gas. As a result, no retention gas is mixed in the exhaust gas 'S' flowing through the gas-introducing pipe 3, and also a turbulence of the exhaust gas S in the gas-introducing pipe 3 can be prevented. That is, the exhaust gas is introduced into the cell 2 in a laminar condition. Accordingly, the exhaust gas generated before and after a particular combustion cycle of the engine 1 can be prevented from being mixed in the exhaust gas generated by the engine both before and after the particular combustion cycle, and thus the exhaust gas 'S' can be immediately introduced into the gas analyzer 2 under the laminar condition.

By way of example, upon introducing the exhaust gas 'S' exhausted from the engine 1 into the gas analyzer 2 without regulating the pressure, a sample inlet port pressure may be changed from about 0 Kgf/cm$^2$ to 1 Kgf/cm$^2$, depending upon an output of the engine 1 and upon the suction rate of the exhaust gas 'S' by the sample-suctioning pump 6. In the case where the analysis cell pressure arrives at, for example, −0.4 Kgf/cm$^2$ from the usual pressure of −0.5 Kgf/cm$^2$, a display on the gas analyzer 2 would be increased by about 20%. This 20% change of indicated quantitative analysis is just as a result of this pressure change, and of the inherent pressure sensitivity of the analysis cell 2, and is not an indication that the quantitative analysis of the gas is truly different. However the change of pressure in the cell 2 at this time is monitored by means of the sensor 7, and the indicated change is compensated by means of the compensating circuit or means 8 on the basis of the monitored pressure.

The indication of gas quantitative analysis is thus made to be unresponsive (in the sense that it is compensate) to pressure fluctuations in the analysis cell, although the analysis cell itself is sensitive to and subject to such fluctuations of pressure. As a result, the exhaust gas generated by the combustion cycles in the engine can be quantitatively analyzed in high response under the condition that an influence by the pressure fluctuations is reduced.

FIG. 2 shows another preferred embodiment suitable in respect of an introduction of a calibration gas 'A' into the gas analyzer cell 2 of the gas-analyzing apparatus. Referring to FIG. 2, reference numeral 20 designates a supply line for the calibration gas 'A'. A supply pipe 9 for the calibration gas 'A' is provided on an outer circumferential portion of the gas-introducing pipe 3 so as to form a double tube together with the gas-introducing pipe 3. A joint pipe 24 for the calibration gas 'A' includes a supply pipe 22 connecting with a source of a zeroing gas, and a pipe 23 connecting with a source of span calibration gas, and each is provided with a respective selectively-operable electro-magnetic valve 21. The joint pipe 24 is connected with a calibration gas inlet port (c) of the supply pipe 9, and a calibration gas outlet port (a) of the supply pipe 9 is projected beyond an exhaust gas inlet port (b) of the gas-introducing pipe 3. As a result, the calibration gas A may be introduced into the gas analyzer 2 through the said exhaust gas inlet port (b). The port (b) is positioned at a depth, or is recessed, relative to the calibration gas outlet port (a).

In addition, the same members as the constituent members shown in FIG. 1 were designated by the same reference numerals as in FIG. 1 and their repeated description is omitted.

According to the present calibration gas-introducing manner, the supply pipe 9 of the calibration gas 'A' is not connected midway the gas-introducing pipe 3 (as would be conventional) so that the calibration gas 'A' may be introduced through the exhaust gas inlet port (b) of the gas-introducing pipe 3. This way of introducing the calibration gas is different from the conventional gas-analyzing apparatus, so that the retention of the calibration gas 'A' in the gas-introducing pipe 3 can be prevented. Also, the turbulence of the exhaust gas 'S' can be prevented as discussed above with respect to the undesirable results of having branch connections and retention volumes connected to the gas-introducing pipe 12. Thus, the quantitatively analysis of the exhaust gas 'S' can be suitably achieved.

Furthermore, the exhaust gas inlet port (b) is positioned in the depth relative to the calibration gas outlet port (a), so that in the calibration gas-introducing process, a circumference of the exhaust gas inlet port (b) of the gas-introducing pipe 3 is shielded with the calibration gas 'A' and thus merely the calibration gas 'A' containing no exhaust gas 'S' can be supplied.

In this connection, in the case where an exhaust gas-introducing pipe 3 having an inside diameter of 2 mm and an outside diameter of 3 mm is used to introduce the exhaust gas into the gas analyzer 2 at a flow rate of 5 liters/min while the supply pipe 9 of the calibration gas 'A' having an inner diameter of 4 mm and an outer diameter of 6 mm is used, its exhaust gas inlet port (b) being positioned in the depth of about 10 mm relative to the calibration gas outlet port (a), and the calibration gas is flowed in at a flow rate of 7 liters/min, merely the calibration gas containing no exhaust gas can be supplied.

As above described, according to the gas-analyzing apparatus of the present invention, rather than the pressure change-regulating solution provided by the conventional art, an electric compensating circuit or means is employed to compensate the indicated change or error on the basis of the change in pressure within an analysis cell. In place of the conventional pressure-regulating means with its branched pipe causing the retention and turbulence of the sample gas, the sample gas is introduced into the gas analyzer under the laminar condition with a gas-introducing pipe substantially free of branch connections and retention volumes. As a result, the exhaust gas generated by a particular combustion cycle of the engine, and the exhaust gas generated before and after the particular combustion cycle can be quantitatively analyzed with high response under the condition that the influence of the pressure fluctuations in the analysis cell is reduced.

What is claimed is:

1. An improved gas analyzer apparatus in which a sample gas is introduced in a laminar condition into a pressure-sensitive analysis cell of the gas analyzer, the gas analyzer apparatus comprising:, a pressure-sensitive analysis cell;

a gas-introducing pipe conveying a sample gas to said analysis cell in a laminar condition, said gas-introducing pipe including an exhaust gas inlet port; and a supply pipe supplying said analyzer cell with a calibration gas, said supply pipe including a calibration gas outlet port projecting beyond said exhaust gas inlet port in a direction opposite said analysis cell and around said exhaust gas inlet port such that said gas-introducing pipe and said supply pipe form a double pipe, said exhaust gas inlet port being positioned at a depth within said supply pipe relative to said calibration gas outlet port.

2. The gas analyzer apparatus of claim 1 including said gas-introducing pipe being substantially free of branch connections thereto.

3. The gas analyzer apparatus of claim 1 including said gas-introducing pipe being of substantially constant sectional shape.

4. The gas analyzer apparatus of claim 1 including said gas-introducing pipe being substantially free of retention volumes communicating thereto.

5. The gas analyzer apparatus of claim 1 wherein said gas-introducing pipe has an inner diameter of about 2 mm and an outer diameter of about 3 mm, said calibration gas supply pipe having an inside diameter of about 4 mm and an outside diameter of about 6 mm, and said calibration supply gas pipe extending beyond the inlet port of said gas-introducing pipe by about 10 mm.

6. The gas analyzer apparatus of claim 1 wherein said calibration gas supply pipe surrounds said gas-introducing pipe throughout substantially the entire length of the latter.

7. An improved exhaust gas analyzer comprising:

an analysis cell which is responsive to both the quantitative analysis of exhaust gasses supplied thereto to provide an output indication of such quantitative analysis, and which is also undesirably responsive to pressure fluctuation of said exhaust gasses such that said output is in error as a result of said pressure fluctuations;

a gas-introducing pipe communicating with a source of exhaust gasses having a fluctuating pressure, said gas-introducing pipe being substantially free both of branch connections and of communication with retention volumes to provide exhaust gasses to said analysis cell in a laminar condition and with pressure fluctuations therein, said gas-introducing pipe including an exhaust gas inlet port; and a calibration gas supply pipe surrounding said gas-introducing pipe for introducing a calibration gas to said analysis cell, said supply pipe including a calibration gas outlet port projecting beyond said exhaust gas inlet port in a direction opposite said analysis cell and around said exhaust gas inlet port such that said gas-introducing pipe and said supply pipe form a double pipe, said exhaust gas inlet port being positioned at a depth within said supply pipe relative to said calibration gas outlet port.

8. The exhaust gas analyzer of claim 7 wherein said calibration gas supply pipe extends beyond said inlet port of said gas-introducing pipe by a distance equal to about five times an inside diameter of said gas-introducing pipe.

9. The exhaust gas analyzer of claim 7 wherein said gas-introducing pipe has an inside diameter of about 2 mm and said calibration gas supply pipe extends beyond said inlet port of said gas-introducing pipe by about 10 mm.

10. The exhaust gas analyzer of claim 7 wherein said gas-introducing pipe has an outside diameter of about 3 mm, and said calibration gas supply pipe has an inside diameter of about 4 mm.

* * * * *